US010215864B2

(12) United States Patent
Herraiz et al.

(10) Patent No.: US 10,215,864 B2
(45) Date of Patent: Feb. 26, 2019

(54) SYSTEM AND METHOD TO IMPROVE IMAGE QUALITY OF EMISSION TOMOGRAPHY WHEN USING ADVANCED RADIONUCLIDES

(71) Applicant: MASSACHUSETTS INSTITUTE OF TECHNOLOGY, Cambridge, MA (US)

(72) Inventors: Joaquikn L. Herraiz, Boston, MA (US); Eduardo M. Lage, Boston, MA (US); Vicente J. Parot, Cambridge, MA (US); Shivang R. Dave, Boston, MA (US)

(73) Assignee: Massachusetts Institute of Technology, Boston, MA (US)

( * ) Notice: Subject to any disclaimer, the term of this patent is extended or adjusted under 35 U.S.C. 154(b) by 646 days.

(21) Appl. No.: 14/902,084

(22) PCT Filed: Jul. 2, 2014

(86) PCT No.: PCT/US2014/045220
§ 371 (c)(1),
(2) Date: Dec. 30, 2015

(87) PCT Pub. No.: WO2015/006123
PCT Pub. Date: Jan. 15, 2015

(65) Prior Publication Data
US 2016/0370474 A1 Dec. 22, 2016

Related U.S. Application Data

(60) Provisional application No. 61/843,800, filed on Jul. 8, 2013.

(51) Int. Cl.
*G01T 1/164* (2006.01)
*A61B 6/03* (2006.01)
*A61B 6/00* (2006.01)

(52) U.S. Cl.
CPC ............ *G01T 1/1647* (2013.01); *A61B 6/037* (2013.01); *A61B 6/4216* (2013.01);
(Continued)

(58) Field of Classification Search
CPC ... G01T 1/1647; A61B 6/4216; A61B 6/5282; A61B 6/5258; A61B 6/4266; A61B 6/037; A61B 6/5205
(Continued)

(56) References Cited

U.S. PATENT DOCUMENTS

| 5,270,923 A | 12/1993 | King et al. |
| 2007/0085013 A1* | 4/2007 | Watson ................. G01T 1/2985 250/363.07 |

(Continued)

OTHER PUBLICATIONS

International Search Report and Written Opinion dated Nov. 7, 2014 in connection with PCT/US2014/045220.

*Primary Examiner* — Sanjay Cattungal
(74) *Attorney, Agent, or Firm* — Quarles & Brady LLP

(57) ABSTRACT

A method and system for acquiring a series of medical images includes a plurality of detectors configured to be arranged to acquire gamma rays emitted from a subject as a result of an advanced radionuclide administered to the subject and communicate signals corresponding to acquired gamma rays. A data processing system is configured to receive the signals from the plurality of detectors, determine double coincidence event dataset and a multiple coincidence event dataset, separate the multiple coincidence event dataset into at least one of a standard lines of response dataset and a nonstandard lines of response dataset, and apply a background correction to the double coincidence event dataset based on the non-standard lines of response dataset and/or the standard lines of response dataset to obtain a standard coincidence dataset.

25 Claims, 4 Drawing Sheets

(52) U.S. Cl.
CPC .......... *A61B 6/4266* (2013.01); *A61B 6/5205* (2013.01); *A61B 6/5258* (2013.01); *A61B 6/5282* (2013.01)

(58) Field of Classification Search
USPC ................................................ 600/407–436
See application file for complete search history.

(56) References Cited

U.S. PATENT DOCUMENTS

| | | | |
|---|---|---|---|
| 2008/0137930 A1* | 6/2008 | Rosen | G06T 11/005 |
| | | | 382/131 |
| 2009/0057561 A1 | 3/2009 | Schweizer et al. | |
| 2010/0116994 A1* | 5/2010 | Wollenweber | G01T 1/1611 |
| | | | 250/363.03 |
| 2010/0230602 A1 | 9/2010 | Scheins | |
| 2011/0147594 A1* | 6/2011 | Scoullar | A61B 6/037 |
| | | | 250/362 |
| 2011/0150181 A1 | 6/2011 | Cook et al. | |
| 2013/0320973 A1* | 12/2013 | Fenchel | A61B 5/055 |
| | | | 324/309 |
| 2014/0046179 A1* | 2/2014 | Olcott | A61B 6/5235 |
| | | | 600/426 |

\* cited by examiner

SYSTEM AND METHOD TO IMPROVE IMAGE QUALITY OF EMISSION TOMOGRAPHY WHEN USING ADVANCED RADIONUCLIDES

CROSS-REFERENCE TO RELATED APPLICATIONS

The present application represents the national stage entry of PCT International Application No. PCT/US2014/045220 filed Jul. 2, 2014, which is based on, and claims priority to, incorporates herein by reference in its entirety, U.S. Provisional Application Ser. No. 61/843,800, filed Jul. 8, 2013, the disclosures of which are incorporated by reference here in their entirety for all purposes.

STATEMENT REGARDING FEDERALLY SPONSORED RESEARCH

N/A

BACKGROUND OF THE INVENTION

The present disclosure relates to systems and methods for emission tomography and, more particularly, to systems and methods for emission tomography that provide an improvement in image quality when using advanced radionuclides, wherein such radionuclides are characterized by the emission of both prompt gamma rays and positrons upon decay.

There are a variety of emission tomography imaging systems and methods. One clinically important example is positron emission tomography (PET) which, generally, utilizes an administered radionuclide (also considered a radioactive isotope or radioisotope) to acquire two-dimensional and three-dimensional tomographic images of a target area or organ of interest in a subject. More specifically, such radionuclides are employed as radioactive tracers called "radiopharmaceuticals" by incorporating them into substances, such as glucose or carbon dioxide. These radiopharmaceuticals are then administered to the patient where they become involved in biological processes such as blood flow; fatty acid and glucose metabolism; and protein synthesis. Through a respective biological process, the radiopharmaceuticals accumulate in, or otherwise target, the area or organ of interest in the subject. By measuring or identifying photons emitted from the area or organ of interest by the accumulated or targeted radiopharmaceutical, clinically useful biological and physiological information can be acquired.

Conventional radionuclides such as fluorine-18 ($^{18}F$), carbon-11 ($^{11}C$), nitrogen-13 ($^{13}N$), and oxygen-15 ($^{15}O$) are commonly used to label PET radiopharmaceuticals. These radionuclides are denominated "conventional" because they decay by emitting only positrons. The positrons travel a very short distance before they encounter an electron and, when this occurs, the positrons are annihilated and converted into two photons, or gamma rays. This annihilation event is characterized by two features that are pertinent to PET imaging. Namely, each annihilation gamma ray has an energy of 511 keV and the two gamma rays are directed in substantially opposite directions. An image is created by determining the number of such annihilation events at each location within the scanner's field of view.

To create such an image, typical PET scanners consist of one or more rings of detectors which are positioned to encircle the subject. Coincidence detection circuits connected to the detectors record only those photons that are detected simultaneously by two detectors located on opposite sides of the subject and that fall within an energy acceptance window around 511 keV. The number of such simultaneous events indicates the number of positron annihilations that occurred along a line joining the two opposing detectors. Within a few minutes, millions of events can be recorded to indicate the number of annihilations along lines joining pairs of detectors in the ring. These numbers are employed to reconstruct an image using well-known tomographic reconstruction techniques.

More specifically, current clinical (and most preclinical) PET scanners and systems include a ring 100 of block detectors 102 for detecting emitted photons, typically in circular, such as the array shown in FIG. 1, or in hexagonal or octagonal arrays. Block detectors 102 include a piece of scintillator material that converts the energy deposited by gamma rays into visible light. The scintillator material is usually segmented into many scintillation crystal elements configured in an array, which is read out by one or more photon detectors (such as a number of individual photomultiplier tubes (PMTs), a position-sensitive photo-multiplier tube (PS-PMT), or silicon photo-multipliers (Si-PM)) that convert the light emitted by the scintillation material into electrical signals whose magnitude is proportional to the energy deposited by the gamma rays in the scintillator material. By combining the output signal of the photon detector(s) of the block detector, it is possible to determine the single crystal in which the detected photon interacted and the energy deposited by such photon.

Furthermore, as shown in FIG. 1, the ring 100 of block detectors of a PET scanner includes individual detectors that are operated in coincidence with a fan beam 104 of block detectors on the opposite side of the ring 100. The inner circle 106 formed by edges of all such fan beams defines the useful field of view. Data is usually recorded simultaneously for all possible fan beams, and the PET scanner will produce an output whenever two photons are detected in opposite block detectors of a fan beam 104 within a specified coincidence timing window (for example, in the range of hundreds of picoseconds to tens of nanoseconds) and when both events fall into a predetermined energy window (usually from 511 keV$-\Delta E_1$ to 511 keV$+\Delta E_2$, where $\Delta E_1$ and $\Delta E_2$ are a function of the energy resolution of the block detectors). Any such events are called double coincidences.

In addition to the conventional radionuclides described above, advanced PET radionuclides (also considered nonstandard radionuclides), for example, such as iodine-124 ($^{124}I$), bromine-76 ($^{76}Br$), yttrium-86 ($^{86}Y$), among others, may be useful for preclinical and clinical studies due to their chemical properties and their relatively long half-life. These properties make them especially well-suited for labeling antibodies, for dosimetry in internal radiotherapy procedures, and for an easy distribution from a cyclotron where they are generated to distant imaging centers. Other advanced radionuclides like rubidium-82 ($^{82}Rb$), which is currently used in cardiac studies, have a short half-life, but can be obtained from a generator, as a decay product of a long half-life parent radionuclide.

Most of these advanced radionuclides, however, have a drawback because, when they decay, prompt gamma rays can be emitted in addition to positrons. This causes the emission of more than two gamma rays per radioactive decay and, as the energy of the additional prompt gamma rays or scattered photons from them may be close to the energy of the standard annihilation gamma rays (that is, about 511 keV), it is difficult to distinguish the prompt gamma rays from the annihilation gamma rays (as the energy resolution of existing PET scanners ranges from about 10% to about 30%). Also, in some cases, the prompt gamma ray has an energy significantly larger than 511 keV, but it may deposit in the detector only part of its energy. If the measured energy is close to about 511 keV, the detected prompt gamma ray cannot be distinguished from the standard gamma rays. As a result, spurious double coincidences may be detected in a conventional PET scanner, causing a significant additional background in reconstructed images, reducing image contrast, decreasing the detectability of hot spots in the images, and compromising their quantitative properties. Such coincidences may be referred to as non-standard spurious coincidences or simply spurious coincidences, for example as opposed to standard coincidences further described below. These coincidences are considered spurious in a spatial or geometrical context, as opposed to a temporal context, because their resulting line of response, described below, does not pass through the point of annihilation.

More specifically, commercial PET scanners are designed to detect and record only double coincidences (as opposed to triple and/or other multiple coincidences that involve the detection, in coincidence, of more than two gamma-rays). The data from these double coincidences are usually stored in a large list of events or in a histogram format (such as a sinogram or line-of-response histograms). When such advanced radionuclides (considered positron plus prompt gamma ray emitters) are used, a number of different events may be detected by the PET scanner. For example, as shown in FIG. 2A, the two annihilation gamma rays A', B' can be detected along their correct line of response (that is, line A-B). This is considered a standard coincidence and, more specifically, a true coincidence (other types of standard coincidences can include random coincidences or in-body scatter coincidences). However, as shown in FIG. 2B, a prompt gamma ray C' can be detected in coincidence with one of the annihilation gamma rays A', resulting in an incorrect, or spurious, line of response (that is, line A-C). This may occur, for example, when gamma ray B' escapes from the scanner gantry or only deposits a portion of its energy at the detector due to scattering, as shown in FIG. 2B, resulting in the scanner not detecting gamma ray B' in coincidence with gamma ray A'. This is considered a non-standard spurious coincidence. Thus, in advanced radionuclide applications, when detected double coincidences are reconstructed using standard reconstruction methods, a significant background in the image can be noticed due to the non-standard spurious coincidences between one annihilation gamma ray and one prompt gamma ray, like that shown in FIG. 2B.

Several methods have been proposed for correcting the spurious activity by estimating the background caused by prompt gamma rays and removing this background during image reconstruction. These methods involve, for example, subtraction of a uniform distribution with an intensity that is obtained using the outer region of the field-of-view (where no real activity is expected to be present) as a reference, modification of the parameters of traditional scatter correction processes, and/or a convolution subtraction method (similar to scatter correction) using either empirically or analytically determined kernel functions. These methods either combine scatter correction and spurious-coincidence-background correction into a single correction assuming a roughly fixed relationship between the two or they try to model the background distribution. Nevertheless, such approaches are often not accurate because the shape of the spurious coincidence distribution can be very different from that of scatter and their relative magnitudes vary with the size, shape, and density of the object being imaged and the radionuclide used.

For example, a first proposed method includes estimating the background created by spurious coincidences by projecting in random directions from points inside measured lines of response. This method obtains an estimation that is later used for subtracting the background from signal data. The limitations of this method are that it requires significant additional computational time for a realistic estimation and that it can fail if the model for the projection is not accurate and not representative of the actual scanner.

In a second proposed method, the first method is combined with a scatter estimation to obtain an additional estimation of the contribution of the spurious background. This method requires some measurement in regions where it is assumed there should be no signal in order to scale the estimation. However, this is not possible for some cases, such as when scanning obese patients that fill the whole or nearly the whole field-of-view of the scanner.

In general, these estimation methods are time-consuming, can introduce bias into the images, depend on the size of the subject, and can affect the statistical properties of the reconstructed images. As a result, they are not effective solutions for improving image quality in PET when using advanced radionuclides and, furthermore, can often have a negative effect on resulting images.

Therefore, it would be desirable to have a system and method to provide a direct measurement of the background caused by prompt gamma rays during PET imaging with advanced radionuclides in order to improve the image quality without relying on inaccurate, time-consuming estimations based on simulations or approximations.

SUMMARY OF THE INVENTION

The present disclosure overcomes the aforementioned drawbacks by providing a system and method for emission tomography that enable the use of data from multiple coincidence events to remove background created by spurious events when using advanced radionuclides. The present disclosure provides a further improvement in scanner performance due to the use of both traditional coincidence data determined from double coincidence events, as well as coincidence data determined from multiple coincidence events. This configuration can be adopted in existing pre-clinical and clinical imaging systems, such as PET scanners, without requiring additional or other non-conventional detector elements.

In accordance with one aspect of the present disclosure, an emission tomography system is disclosed for acquiring a series of medical images of a subject after administration of radionuclides that emit positrons and prompt gamma rays. The system includes a plurality of detectors configured to be arranged about the subject to acquire gamma rays emitted from the subject as a result of the radionuclide administered to the subject and communicate signals corresponding to acquired gamma rays. The system also includes a data processing system configured to receive the signals from the plurality of detectors and determine a double coincidence event dataset and a multiple coincidence event dataset. The data processing system is also configured to separate the multiple coincidence event dataset into a standard lines of response dataset and a non-standard lines of response dataset and apply a correction to the double coincidence event dataset based on at least the non-standard lines of response dataset to obtain a standard coincidence dataset. The system further includes a reconstruction system configured to receive the standard coincidence dataset and reconstruct therefrom a series of medical images of the subject.

In accordance with another aspect of the present disclosure, a method for acquiring a series of medical images of a subject is disclosed. The method includes providing a radionuclide to a subject, detecting photons emitted from the subject in response to the radionuclide administered to the subject, creating imaging data based on the detected photons, processing the imaging data to identify double coincidence events and multiple coincidence events associated with the detected photons, and mapping the double coincidence events and the multiple coincidence events into a double coincidence event dataset and a multiple coincidence event dataset, respectively. The method further includes extracting at least one of a spurious lines of response dataset and a standard lines of response dataset from the multiple coincidence dataset, applying a background correction to the double coincidence event dataset based on at least one of the spurious lines of response dataset and the standard lines of response dataset to obtain a standard coincidence dataset, and reconstructing a series of medical images of the subject using the standard coincidence dataset.

In accordance with yet another aspect of the present disclosure, an emission tomography system is disclosed for acquiring a series of medical images of a subject after administration of radionuclides that emit positrons and prompt gamma rays. The system includes a plurality of detectors configured to be arranged about the subject to acquire gamma rays emitted from the subject as a result of the radionuclide administered to the subject and communicate signals corresponding to acquired gamma rays. The system also includes a data processing system configured to receive the signals from the plurality of detectors and determine a double coincidence event dataset and a multiple coincidence event dataset. The data processing system is also configured to separate the multiple coincidence event dataset into at least one of a standard lines of response dataset and a non-standard lines of response dataset and obtain a correction for the double coincidence event dataset based on at least one of the standard lines of response dataset and the non-standard lines of response dataset. The system further includes a reconstruction system configured to receive the double coincidence dataset and the correction and reconstruct therefrom a series of medical images of the subject.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

In general, modern positron emission tomography (PET) systems provide quantitative images of a distribution of injected radiolabeled molecules of interest within a subject. The fact that PET images are quantitative is one of its major advantages compared to other medical imaging modalities. The precise measurement of a radiotracer present in a specific region, like a tumor, is useful for both clinical and research purposes. However, a significant problem arises when advanced radionuclides are used in a PET system, as the background generated by spurious coincidences decreases image contrast and may yield to wrong quantitative measurements. As will be described, the present disclosure overcomes these drawbacks by providing a system and method for PET that allows for improved image quality and increased system sensitivity without additional hardware requirements or excessive computation time. The methods of the present disclosure rely on measurements obtained by the PET system rather than models or estimations. As a result, the present disclosure not only provides a faster method to remove the background in PET images, but is also less prone to bias or errors. Generally, methods of the present disclosure include measuring multiple (that is, triple or greater) coincidences and using these multiple coincidences to separate a signal and spurious contributions. Using the signal and/or the spurious contributions, traditionally measured double coincidences are corrected and enhanced to allow for reconstructed images with improved image quality and contrast as well as improved system sensitivity.

Typically, PET scanners detect and record only double coincidence events, while triple coincidences or, more generally, multiple coincidence events which include detecting more than two gamma-rays simultaneously, are not recorded or used during image reconstruction. As an improvement to current PET technology, N-tuples coincidences (N≥2) corresponding to N events detected within a narrow time coincidence window can be recorded by a modified version of current PET, PET/CT, PET/MRI, or other scanners or by new or future systems designed with this capability. In other words, such a modification allows for double coincidence events and multiple (N>2) coincidence events to be detected. The modifications can involve using a modified version of hardware and/or acquisition software, as well as new designs specifically suited for such additional detections.

Figure 1:
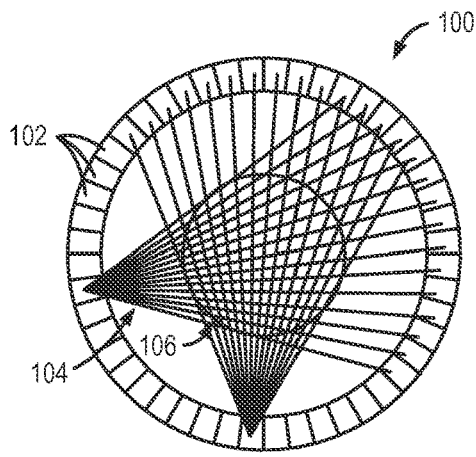
FIG. 1 is a schematic view of a ring of block detectors in a positron emission tomography (PET) system.
Figure 2A:
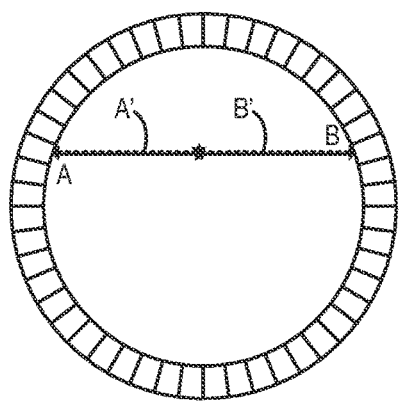
FIGS. 2A-2C are schematic views of coincidence events in a PET system, including a standard coincidence event (FIG. 2A), a non-standard spurious coincidence event (FIG. 2B), and a multiple coincidence event (triple coincidence, in this case) including both standard and non-standard spurious coincidences (FIG. 2C).
Figure 2B:
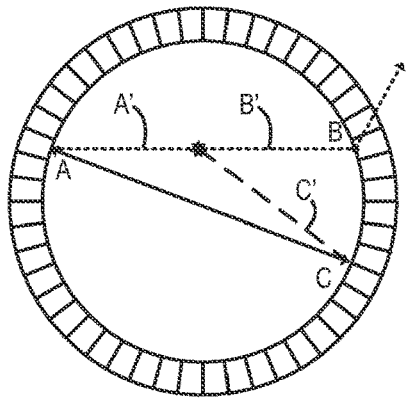
Figure 2C:
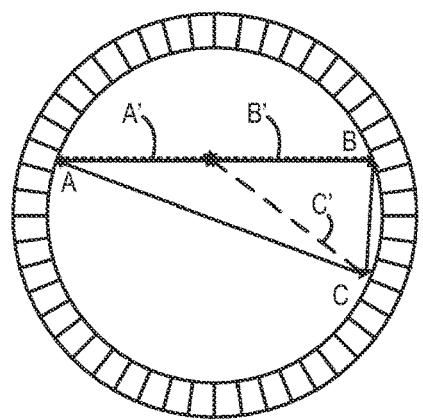

The present disclosure recognizes that the detection and use of multiple coincidence events can improve the quality of reconstructed images when using, for example, advanced radionuclides. Examples of advanced PET radionuclides may include iodine-124 ($^{124}$I,) bromine-76 ($^{76}$Br), yttrium-86 ($^{86}$Y), rubidium-82 ($^{82}$Rb), and others that can emit both prompt gamma rays and positrons as they decay. When such advanced radionuclides are used, a number of different events may be detected by the PET scanner. For example, as shown in FIG. 2A, two annihilation gamma rays A', B' can be detected as a double coincidence along their true line of response (that is, line A-B). As shown in FIG. 2B, a prompt gamma ray C' can be detected in coincidence with one of the annihilation gamma rays A', resulting in a double coincidence along a spurious line of response (that is, line A-C). Standard coincidences, such as that shown in FIG. 2A, produce valid information, while non-standard spurious coincidences, such as that shown in FIG. 2B, produce distorted information. In particular, spurious coincidences yield incorrect positional information and contribute to background in the reconstructed image, which results in a loss of contrast and quantitative accuracy. In addition to the two events illustrated in FIGS. 2A and 2B, a triple coincidence may be detected. For example, as shown in FIG. 2C, three gamma rays A', B', C' can be detected as a triple coincidence, where the three possible lines of response from this triple coincidence (that is, line A-B, line B-C, and line A-C) are a mixture of standard and non-standard spurious double coincidences.

Generally, a scanner capable of N-tuples detection (that is, double coincidence, triple coincidence, and the like) can provide N−1 separate datasets corresponding to each N-tuple coincidence type. The data points in a particular dataset include all relevant information (such as localization and energy) of each of the N-events comprising the N-tuple coincidence. This information is then encoded in a more compact format by using, for instance, the number of the lines of response (LORs) or sinogram bins that can be obtained from all allowed combinations of pairs of detected events.

For example, one dataset can contain double coincidences, each one associated to a specific LOR or sinogram bin. The coincidence events in FIGS. 2A and 2B would fall into this dataset with line A-B and line A-C, respectively, as the lines of response. Another dataset can contain triple coincidences, each one associated with three LORs or sinogram bins. In some cases, due to geometric constraints, one of the possible lines of response may lie outside of the field of view and therefore can be discarded (that is, because it does not correspond to a valid line of response or sinogram bin). As a result, a triple coincidence may be associated only to two LORs or sinogram bins. Accordingly, the coincidence event in FIG. 2C would fall into this dataset with line A-B and line A-C as the possible lines of response (line B-C would be discarded because it lies outside the field of view).

Figure 3:
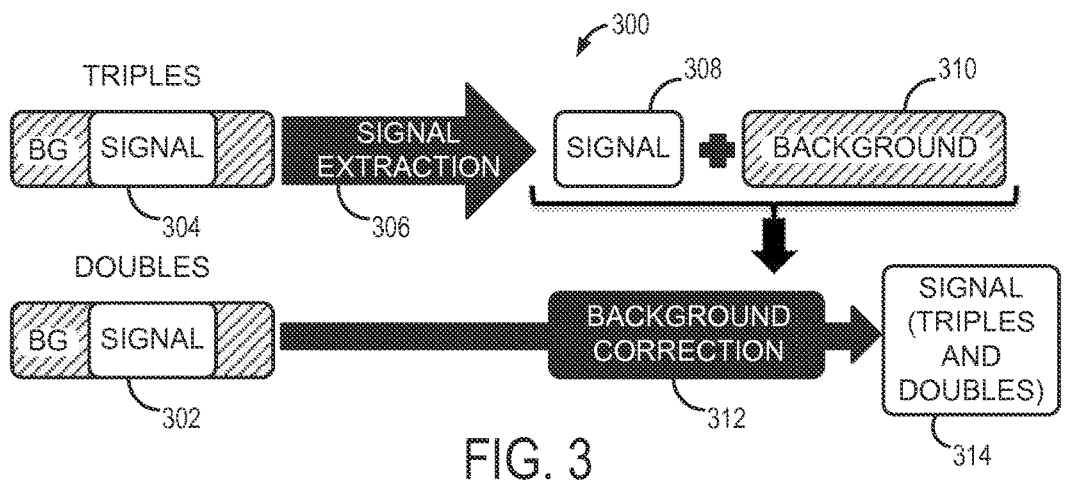
FIG. 3 is a schematic diagram illustrating a background correction method in accordance with the present disclosure.

The above-described datasets each include standard coincidences (such as true, scatter, and/or random double coincidences) as well as non-standard spurious coincidences. As discussed above, such spurious coincidences contribute to produce additional background in resulting generated images. The present disclosure provides a method for utilizing multiple coincidences to measure this background and apply a background correction to eliminate or reduce such background from the double coincidence dataset and, thus, reduce the background in resulting generated images. This method 300 is generally illustrated in FIG. 3. As shown in FIG. 3, a double coincidence dataset (process block 302) includes a signal (that is, standard true, scatter, and random coincidences) and an additional background (that is, spurious coincidences). A multiple, that is, triple coincidence dataset (process block 304) also includes background (spurious coincidences) and a signal.

From the triple coincidence dataset, it is known that only one of the lines of response that compose the triple coincidence corresponds to the right or correct LOR and the others correspond to the same type of spurious background present in the double coincidences. Using an iterative procedure (at process block 306, described in further detail with respect to FIG. 4), from the triple coincidence detections (such as that shown in FIG. 2C), a separate measurement of the signal (standard coincidences, at process block 308) and the spurious background (non-standard spurious coincidences such as that shown in FIG. 2B, at process block 310) is obtained. This separated signal and/or background is then used to apply a background correction to the double coincidence dataset (at process block 312) to achieve a signal (at process block 314) with reduced or controlled spurious additional background. Additionally, the separated signal from the triple coincidence dataset can be combined with the signal from the double coincidence dataset to improve the sensitivity, reducing the noise. Images can be reconstructed using this combined signal, wherein such images have higher quality and better contrast in comparison to images corrected through other methods.

Figure 4:
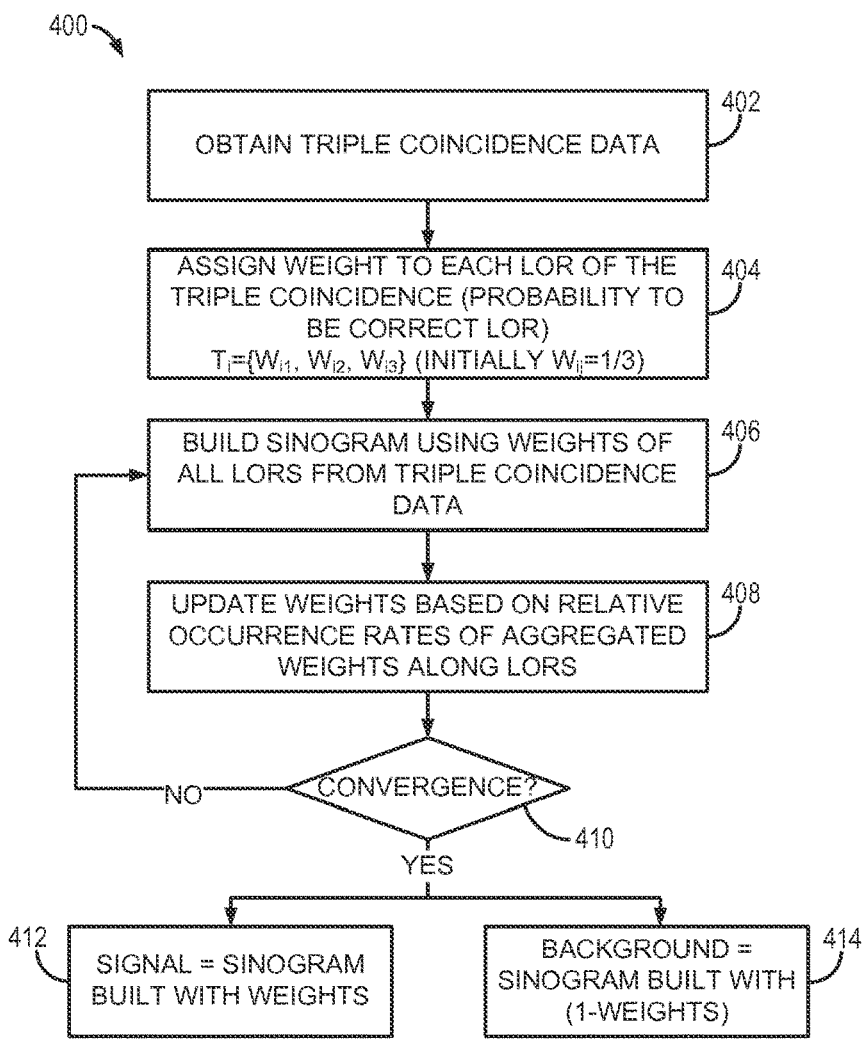
FIG. 4 is a flow chart setting forth the steps of a background separation method in accordance with the present disclosure.

FIG. 4 illustrates a method 400 according to the present disclosure for signal and background separation (or extraction) from a triple coincidence dataset. This method 400 can correspond to process blocks 306-310 of the method 300 illustrated in FIG. 3. As shown in FIG. 4, at process block 402, triple coincidence data are obtained. At process block 404, weights are applied to each line of response in a particular triple coincidence. These weights may represent the probability of each of these lines to be the right or standard line of response. For example, each triple coincidence, "i", may be composed of three lines of response $LOR_{i1}$, $LOR_{i2}$, $LOR_{i3}$, each one with weights $w_{i1}$, $w_{i2}$, $w_{i3}$, as illustrated in Equation 1 below:

$$\text{Triple}_i = \{(w_{i1}, LOR_{i1}), (w_{i2}, LOR_{i2}), (w_{i3}, LOR_{i3})\},$$
$$i = 1 \ldots N_{Triples} \quad \text{(Eq. 1)}$$

If no additional information is available, the weights of $w_{i1}$, $w_{i2}$, $w_{i3}$ are initially each set to one-third. If one of the lines of response, for instance $LOR_{i3}$, is not valid due to geometrical reasons (for example, line B-C of FIG. 2C), $w_{i1}$ and $w_{i2}$ may be both set to 0.5 and $w_{i3}$ is set to 0. At process block 406, each weighted line of response is added as another count or partial count (based on its weight) in a corresponding bin within a sinogram (or LOR histogram). These weights can also be modified to take into account information like the energy and/or location of each detected event or timing information (such as the time-difference between detections, if available). Then, at process block 408, the total value in each sinogram bin is used to modify the LOR weights. More specifically, the LOR weights can be modified based on relative occurrence rates of aggregated weights along each LOR. For example, weights can be modified according to the following equation:

$$w_{ij} = \frac{N_{ij}}{N_{i1} + N_{i2} + N_{i3}}, \, , i = 1 \ldots N_{Triples}, \quad \text{(Eq. 2)}$$

where $N_{ij}$ represents the occurrence rate for the $LOR_{ij}$ in the sinogram. Other criteria for the weights are also possible in accordance with methods of the present disclosure.

After all the weights have been updated at process block 408, a new sinogram is created based on these new weights (at process block 406), and the procedure is repeated until convergence (that is, no significant further changes in weights between consecutive iterations), as determined at process block 410. In some applications, this may require two, three, or more iterations. In other applications, this may require tens of iterations. Following convergence determination at process block 410, the resulting sinogram including the final weights $w_{ij}$ represents a signal dataset (a standard lines of response dataset, at process block 412). In addition, a secondary sinogram can be constructed using complementary weights $(1-w_{ij})$, to represent a spurious background dataset (a non-standard lines of response dataset, at process block 414).

The separated signal and background datasets may then be used to apply background correction to a double coincidence dataset and also to reduce the noise in the double coincidence dataset, thus resulting in a corrected double coincidence dataset (a standard coincidence dataset). Background correction can be performed in different ways such as, for example, by scaling and subtracting spurious non-standard coincidences using the spurious background dataset or inside an iterative reconstruction procedure. Scaling may be necessary in some applications to relate the number of double coincidences to the number of triple coincidences and, in such applications, a scaling factor may be known a priori or obtained from the data itself. In another example, background correction includes estimating the corrected double coincidence dataset in an iterative fashion based on both the double coincidence dataset and the background dataset. In yet another example, background correction includes estimating the corrected double coincidence dataset in an iterative fashion based on both the double coincidence dataset and the signal dataset extracted from the multiple coincidence dataset (that is, a complementary method with respect to the other example described above). Additionally, the signal dataset can be added to the corrected double coincidence dataset to increase the sensitivity of the acquisition. Accordingly, the methods 300, 400 of FIGS. 3 and 4 can be used to provide an accurate measurement of the spurious background distribution and separate such distribution from the signal. These methods 300, 400 require less computing time than other proposed methods that estimate this background based on a number of assumptions. Furthermore, these methods 300, 400 provide additional valid coincidence data (that is, from the signal dataset) to the final signal used in reconstruction, thereby increasing the sensitivity of the acquisition.

In addition, as described above, when the system is capable of different types of multiple coincidence detection, such as a first n-tuple multiple coincidence and a second (n+1)-tuple coincidence, where n>2, separate datasets corresponding to each multiple coincidence type are provided. In such applications, signal and background separation can be performed for each of the datasets. Separate background corrections or a cumulative background correction can then be applied to the double coincidence dataset based on the backgrounds and/or signals extracted from each of the multiple coincidence datasets. Furthermore, signal extracted from each of the multiple coincidence datasets can be added to the double coincidence dataset to further improve the sensitivity of the acquisition.

Figure 5:
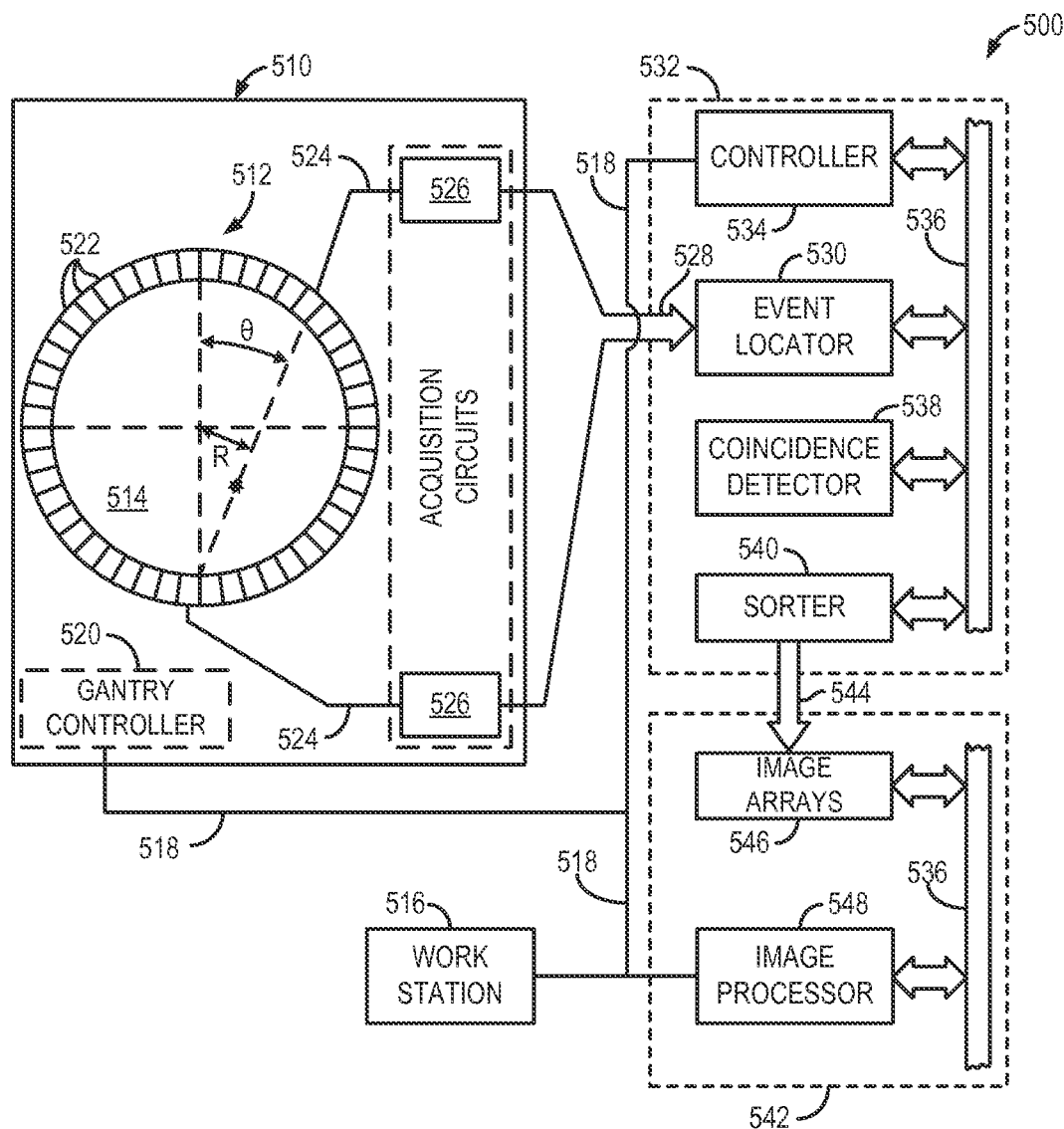
FIG. 5 is a schematic view of a PET system in accordance with the present disclosure.

As described above, methods of the present disclosure may be particularly useful for improving image quality in imaging systems with radiation detectors including, but not limited to, standard (that is, scintillator-type) clinical and preclinical PET systems or other clinical and preclinical PET systems. FIG. 5 illustrates an example PET system 500 for use with the present disclosure. The following paragraphs describe the components of the PET system 500 of FIG. 5 with respect to methods of the present disclosure.

The detector ring assembly 512 is formed of a multitude of radiation detector units 522, represented in this example as block detectors. Each radiation detector unit 522 may include a set of scintillator crystals that is disposed in front of an array of photomultiplier tubes or a position-sensitive photomultiplier tube (not shown), or may be any other suitable radiation detector (for example, such as a high granularity detector). Each radiation detector 522 produces a signal responsive to detection of a photon on communications line 524 when an event occurs. A set of acquisition circuits 526 receive the signals and produce signals indicating the event coordinates (x, y) and the total energy associated with the photons that caused the event. These signals are sent through a cable 528 to an event locator circuit 530. Each acquisition circuit 526 also obtains information from the detector's signals that indicates the exact moment the event took place. For example, with scintillator-type block detectors, sophisticated digital electronics can obtain this information regarding the precise instant in which the scintillations occurred from the samples of the signals used to obtain energy and event coordinates.

The event locator circuits 530, in some implementations, form part of a data acquisition processing system 532 that processes the signals produced by the acquisition circuits 526. The data acquisition processing system 532 usually includes a general controller 534 that controls communications, for example, by way of a backplane bus 536 and on the general communications network 518. The event locator circuits 530 assemble the information regarding each valid event into a set of numbers that indicate precisely when the event took place, the position in which the event was detected and the energy deposited by the photon. This event data packet is conveyed to a coincidence detector 538 that is also part of the data acquisition processing system 532.

The coincidence detector 538 accepts the event data packets from the event locator circuit 530 and determines if any two of them are in coincidence. Coincidence is determined by a number of factors. First, the energy associated with each event data packet must fall within a predefined energy acceptance window, such as around 511 keV (for example, 511 keV$-\Delta E_1$ to 511 keV$+\Delta E_2$, where $\Delta E_1$ and $\Delta E_2$ are chosen as a function of the energy resolution of the radiation detector units). Second, the time markers in each event data packet must be within a predetermined time window, for example, 5 nanoseconds or even down to picoseconds. Third, the locations indicated by the two event data packets must lie on a straight line that passes through the field of view in the scanner bore 514. Coincidences that fall under these factors can be considered double coincidences, including standard coincidences (such as the true coincidence shown in FIG. 2A) and non-standard spurious coincidences (as shown in FIG. 2B). Traditionally, events that cannot be paired are discarded from consideration by the coincidence detector 538, but coincident event pairs are located and recorded as a coincidence data packet. This coincidence data packet, which constitutes traditional PET data, will be referred to as dataset 1.

In accordance with the present disclosure, the coincidence detector 538 may perform the above-described functionality of a traditional PET system, but can also determine if any three or more event data packets are in coincidence (that is, as a triple coincidence or, in general, a multiple coincidence). Such events may correspond to photon events with energy deviating from the standard 511 keV of an electron-positron annihilation event. These triple coincidence events can be located and recorded as another coincidence data packet, which will be referred to as dataset 2.

Dataset 1, dataset 2, and other acquired data (including non-coincidence data and/or other data) are provided to a sorter 540. The function of the sorter in many traditional PET imaging systems is to receive the coincidence data packets and generate memory addresses from the coincidence data packets for the efficient storage of the coincidence data. In that context, the set of all projection rays, or lines of response, that point in the same direction (θ) and pass through the scanner's field of view (FOV) is a complete projection, or "view". The distance (R) between a particular line of response and the center of the FOV locates that line of response within the FOV. The sorter 540 counts all of the events that occur on a given line of response (R, θ) during the scan by sorting out the coincidence data packets that indicate an event at the two detectors lying on this line of response. Because triple coincidence events involve more than two detectors, such events may be counted on one or more given lines of response (that is, a subset of lines of response), as described above.

Once all events are counted, the coincidence counts are organized, for example, as a set of two-dimensional arrays, one for each axial image plane, and each having as one of its dimensions the projection angle θ and the other dimension the distance R. This θ by R map of the measured events is call a histogram or, more commonly, a sinogram array. As further described below, dataset 1 and dataset 2 can be processed and corrections may be applied to obtain a final dataset. The sinogram of the final dataset can be processed to reconstruct images that indicate the true number of events that took place at each image pixel location during the scan. The sorter 540 counts all events occurring along each line of response (R, θ) of this final dataset and organizes them into an image data array.

The sorter 540 provides the image dataset array to an image processing/reconstruction system, for example, by way of a communications link 544 to be stored in an image array 546. The image array 546 holds the dataset array for access by an image processor 548 that reconstructs one or more images corresponding to the dataset array.

Figure 6:
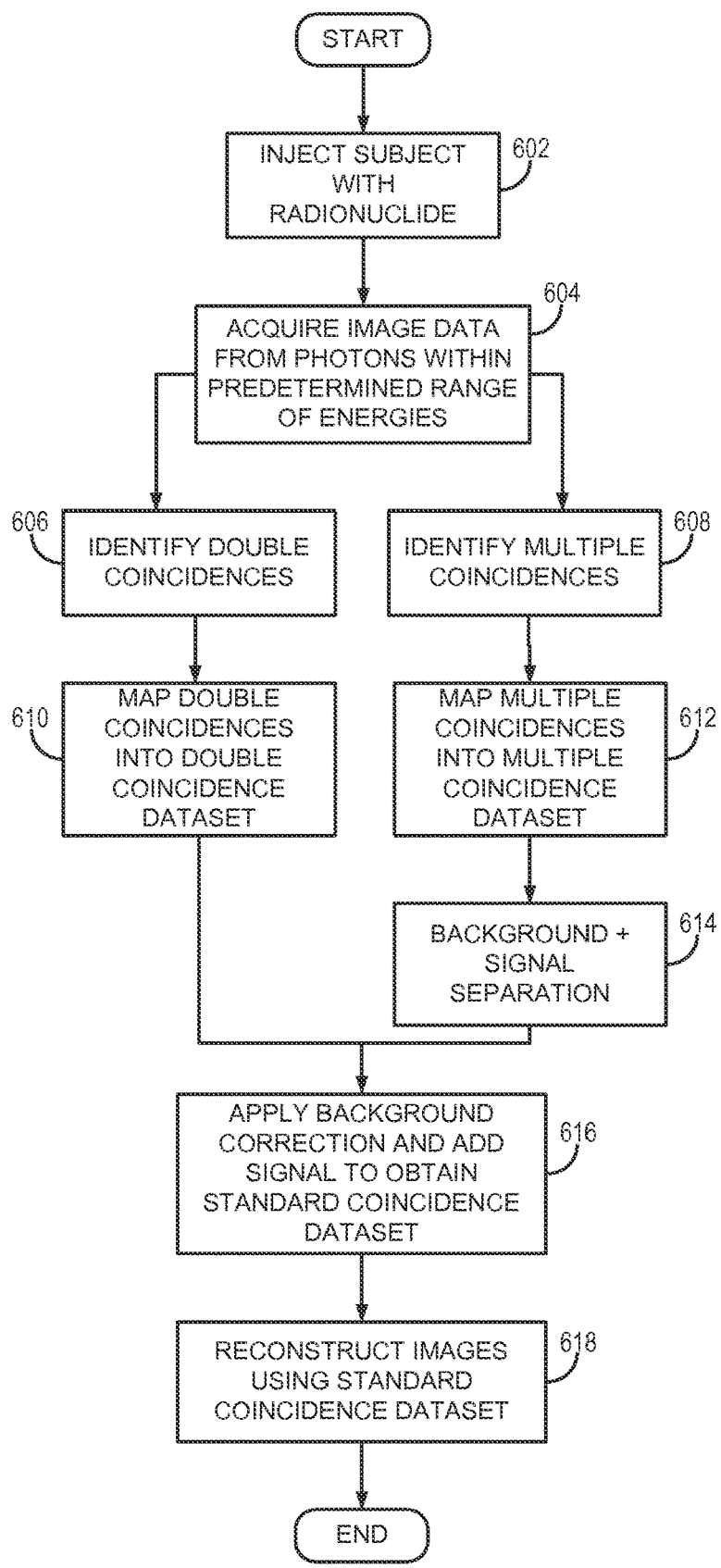
FIG. 6 is a flow chart setting forth the steps of a method of using a PET system in accordance with the present disclosure.

Referring now to FIG. 6, and with reference to the PET system 500 described above, a process 600 for acquiring image data and creating images in accordance with the present disclosure will be described. More specifically, FIG. 6 illustrates a PET imaging process for use with advanced radionuclides. Though described with reference to the PET system 500, this process 600 may be executed on any conventional emission tomography system, such as those including scintillator-type block detectors. This process 600 may also be executed in tomography systems using high-granularity detectors or other specific configurations.

Generally, the process 600 begins at process block 602 with the administration of an advanced radionuclide, such as those described above, to a subject, followed by process block 604 with the acquisition of image data. Next, at process blocks 606 and 608, double (two-photon) coincidences and triple (three-photon) coincidences, respectively, are identified. As discussed above, a two-photon coincidence can include a standard coincidence or a non-standard spurious coincidence. Triple coincidences, in many cases, are indicative of a standard coincidence plus one or two non-standard spurious coincidences as a result of prompt and annihilation gamma rays emitted as the radionuclide decays (a smaller amount of triple coincidences may also result from interdetector scatter or random triple coincidences). For sake of clarity, triple coincidence events are described herein; however, the process 600 can be applied to other multiple coincidences (that is, four-photon, five-photon, . . . , n-photon coincidences). At process block 610, the double coincidences are processed and respective lines of response are mapped in a double coincidence dataset, and, at process block 612, the triple photon coincidences are processed and all possible lines of response are mapped in a triple coincidence dataset.

At process block 614, an iterative signal and background separation process (such as that described above with respect to FIG. 4 or another suitable method) is applied to the triple coincidence dataset to separate the triple coincidence dataset into signal (a standard lines of response dataset corresponding to standard coincidences) and background (a non-standard lines of response dataset corresponding to spurious coincidences). At process block 616, a background correction is applied to the double coincidence dataset based on the background distribution and/or the signal distribution determined at process block 614 (that is, to remove spurious coincidences from the double coincidence dataset). In addition, at process block 616, the signal determined at process block 614 can be added to the double coincidence dataset. The application of background correction, and a possible addition of the triple coincidence signal, results in a final standard coincidence dataset, which is different than the double coincidence dataset in that spurious coincidences are removed and more standard coincidences, including more true coincidences (which would typically have been discarded) are added. At process block 618, a set of images is reconstructed based on the standard coincidence dataset.

More specifically, referring back to process block 604, image data is acquired by detecting and recording N-photon coincidences within a coincidence window, for example on the order of picoseconds to nanoseconds, in different detectors of the scanner and across a predetermined range of energies. That is, a wide range of image data is collected to ensure that data for each annihilation event, including prompt gamma rays that deposit energies above the standard 511 keV, is acquired. In other words, in order to detect and register three photon coincidences (that is, to accept prompt gamma rays and annihilation gamma rays), a PET scanner may be configured to employ a wider energy acceptance window than the one commonly used in clinical and preclinical scanners. Since the energy window in current scanners is a narrow band around 511 keV, detected events such as from gamma ray C' shown in FIG. 2C may be discarded by the software or hardware of the scanner. Accordingly, the energy window can be widened based on the specific radionuclide administered. With reference to the PET system 500 described above, process block 604 can be executed by the acquisition circuits 526 and the event locator circuits 530 assembling detection signals produced by detector units 522 into event data packets that indicate when each event took place, the position in which each event was detected, and the energy deposited by each event.

At process block 606 and process block 608, double coincidences and triple coincidences, respectively, are identified. Double coincidences can be detected by a conventional set of factors, as described above, while triple coincidences can be detected by a separate set of factors. The set of factors used to detect triple coincidences can include some factors similar to those required for coincident event pairs, for example wherein the time markers in each event data packet must be within a predetermined time window, such as 5 nanoseconds or even down to picoseconds, and the locations indicated by at least the two of the three event data packets must lie on a straight line that passes through the field of view. However, the following additional factors may be required for triple coincidences that are not necessary for traditional coincidence pairs.

For example, a triple coincidence may be identified when, first, three events are identified within a first, predetermined coarse time window such as 10 nanoseconds, or even down to single nanoseconds. Second, of those three events, exactly two lines of response cross the field of view and, for each of the two lines of response, a time difference between the two events that define such line of response is identified within a second, predetermined fine time window such as 2 nanoseconds, or even down to picoseconds. In addition, other factors can be related to the energy of the prompt gamma rays emitted by the advanced radionuclide. For example, if the prompt gamma ray is of 650 keV, triple coincidences can be selected using events in which two photons are in an energy window of 511 keV$-\Delta E_1$ to 511 keV$+\Delta E_2$, and the remaining photon is in an energy window of 650 keV$-\Delta E'_1$ to 650 keV$+\Delta E'_2$ (where $\Delta E_1$, $\Delta E'_1$, $\Delta E_2$, and $\Delta E'_2$ are a function of the energy resolution of the detectors).

In addition, triple coincidences may be recovered from a total set of coincidences registered by the PET system 500 (that is, from the acquired image data), as some manufacturers register detected multiple coincidences as a set of all possible double coincidences. More specifically, many current clinical PET systems store multiple coincidence data in standard list-mode files as two or three consecutive (or quasi-consecutive) LORs with a common single event. In other words, detected consecutive double coincidence pairs can be grouped based on, among other factors, whether they share a common radiation detector (for example, detected lines A-B and A-C in FIG. 2B share a common radiation detector at A). Thus, a triple coincidence may be identified as a group including a first double coincidence and a second double coincidence that share a common radiation detector (or event), where the first and second double coincidences are consecutive or near-consecutive. Accordingly, in some cases, multiple coincidences can be extracted offline from this standard list-mode data without making any changes to hardware or software of current clinical PET systems.

With reference to the PET system 500 described above, process blocks 606 and 608 can be executed by the coincidence detector 538, where data event packets are accepted, analyzed, and double coincidences are recorded in a first coincidence data packet, referred to as dataset 1, and triple coincidences are recorded in a second coincidence data packet, referred to as dataset 2. In some applications, dataset 2 comprises groups of double coincidences, as described above.

At process block 610, the double coincidences (that is, dataset 1) are processed and mapped along their respective lines of response in accordance with conventional sorting methods. At process block 612, the triple coincidences (that is, dataset 2) are processed and mapped using multiple weighted lines of response, as described above. At process block 614, a signal and background separation process, such as that illustrated in FIG. 4, is applied to dataset 2 to separate standard coincidences (signal) from spurious background in dataset 2. This can result in a standard lines of response dataset (corresponding to signal) and a non-standard lines of response dataset (corresponding to background). At process block 616, a background correction is applied to dataset 1 based on the background (and/or the signal) determined at step 614, as described above with reference to FIGS. 3 and 4. In addition, at process block 616, the signal determined in process block 614 can be combined with dataset 1. As a result, a standard coincidence dataset with lower noise and reduced background is obtained. At this point, it is also possible to apply conventional, standard corrections to the standard coincidence dataset, such as scatter or random corrections, in order to increase the signal to noise ratio (that is, true coincidences compared to the sum of in-body scattered and random coincidences).

With reference to the PET system 500 described above, process blocks 610, 612, 614, and 616 can be executed by the sorter 540. All counted events along the lines of response from the standard coincidence dataset can be organized into a single image dataset array to be stored in the image array 546. In addition, though not shown in FIG. 6, in some applications, process blocks 608-610 can be repeated (for example, performed concurrently) for other multiple coincidence events, such as four-photon events, five-photon events, etc., and background and signal separated from these other multiple coincidence datasets can be applied at process block 616.

At process block 618, a set of images is reconstructed using the standard coincidence dataset. With reference to the PET system 500 described above, process block 618 can be executed by the image processor 548, where the image dataset array, held by the image array 546, is processed and reconstructed into an image or a series of images corresponding to the image dataset array. In addition, in some applications, process blocks 616 and 618 can be combined so that background correction is applied through an iterative reconstruction process. For example, in such applications, the image processor 548 can receive as inputs the double coincidence dataset (the original dataset or an enhanced dataset with the signal from process block 614) and the background from process block 614. The image processor 548 therefore processes the inputs and reconstructs an image or a series of images therefrom using an iterative reconstruction process.

Accordingly, images are reconstructed based on both double coincidence data as well as triple coincidence data, wherein the triple coincidence data is used to remove spurious background as well as add more standard coincidence events (including more true coincidence events) to the double coincidence data. Thus, the use of triple coincidence events during image reconstruction can result in images with an increased number of true events and a decreased number of spurious events and, consequently, increased signal to noise ratio (SNR) and increased contrast to noise ratio (CNR). More specifically, because the additional true events and reduced spurious events, which are determined from data that is traditionally thrown out, can be used to reconstruct the images, an emission tomography system using this method provides a better image quality and has a higher sensitivity in comparison to conventional PET systems. Furthermore, the use of triple coincidence data to accurately determine spurious background distribution enables faster, as well as more accurate, image reconstruction and processing in comparison to other methods.

Thus, the methods described herein provide an improvement in image quality and sensitivity when using advanced radionuclides, and such methods can be adopted in existing preclinical and clinical PET scanners without requiring any hardware modifications. For example, traditionally, performance parameters are very similar among commercially available PET scanners with similar hardware, and there is an almost linear trend between the quantity of detector material used in the scanner, its sensitivity, and its price. However, the present disclosure can provide a competitive advantage to current commercially available scanners, since sensitivity and image quality can be improved using data that is readily available without requiring additional materials and, thus, additional material costs. Furthermore, the present disclosure can provide a competitive advantage over existing background correction methods due to faster computation and more accurate correction without the need for additional hardware.

The present invention has been described in terms of one or more preferred embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. An emission tomography system for acquiring a series of medical images of a subject after administration of a radionuclide to the subject, wherein the radionuclide decays emitting positrons and at least one prompt gamma ray, the system comprising:
   a plurality of detectors configured to be arranged about the subject to acquire gamma rays emitted from the subject as a result of the radionuclide administered to the subject and communicate signals corresponding to acquired gamma rays;
   a data processing system configured to
      receive the signals from the plurality of detectors,
      determine, from the signals from the plurality of detectors, a double coincidence event dataset and a multiple coincidence event dataset,
      separate the multiple coincidence event dataset into a standard lines of response dataset and a non-standard lines of response dataset,
      apply a correction to the double coincidence event dataset based on at least one of the non-standard lines of response dataset and the standard lines of response dataset to obtain a standard coincidence dataset; and
   a reconstruction system configured to receive the standard coincidence dataset and reconstruct therefrom a series of medical images of the subject.

2. The system of claim 1 wherein separating the multiple coincidence event dataset into the standard lines of response dataset and the non-standard lines of response dataset includes:
   identifying multiple coincidence events comprising at least two lines of response in a field of view of the subject,
   applying weights to each of the at least two lines of response,
   updating the weights based on relative occurrence rates of aggregated weights along each of the at least two lines of response,
   determining the standard lines of response dataset as a distribution of the at least two lines of response with the updated weights applied, and
   determining the non-standard lines of response dataset as a distribution of the at least two lines of response with a complement of the updated weights applied.

3. The system of claim 2, wherein the weights are selected based on probabilities that a standard coincidence event lies along the corresponding line of response.

4. The system of claim 2, wherein the weights are updated in an iterative process until convergence is achieved.

5. The system of claim 2, wherein applying the correction includes scaling and subtracting the non-standard lines of response dataset from the double coincidence event dataset.

6. The system of claim 2, wherein applying the correction includes estimating the standard coincidence dataset in an iterative fashion based on the double coincidence dataset and the non-standard lines of response dataset.

7. The system of claim 2, wherein applying the correction includes estimating the standard coincidence dataset in an iterative fashion based on the double coincidence dataset and the standard lines of response dataset.

8. The system of claim 2, wherein the complement of the updated weights is obtained as one minus the updated weights.

9. The system of claim 1 and further comprising adding the standard lines of response dataset to the standard coincidence dataset.

10. The system of claim 1, wherein the multiple coincidence event dataset includes data corresponding to N-tuple coincidence events, wherein N is greater than two.

11. The system of claim 1, wherein the multiple coincidence event dataset is a triple coincidence event dataset.

12. The system of claim 1, wherein the multiple coincidence event dataset is comprised of groups of double coincidence events, wherein each group is at least comprised of a first double coincidence and a second double coincidence that share a common radiation detector.

13. The system of claim 1, wherein the correction is a background correction.

14. A method for acquiring a series of medical images of a subject, the method comprising:
   providing a radionuclide to a subject;
   detecting photons emitted from the subject in response to the radionuclide administered to the subject;
   creating imaging data based on the detected photons;
   processing the imaging data to identify double coincidence events and multiple coincidence events associated with the detected photons, wherein multiple coincidence events are characterized by more than two photons in coincidence;
   mapping the double coincidence events into a double coincidence event dataset;
   mapping the multiple coincidence events into a multiple coincidence event dataset;
   extracting at least one of a spurious lines of response dataset and a standard lines of response dataset from the multiple coincidence event dataset;
   applying a correction to the double coincidence event dataset based on at least one of the spurious lines of response dataset and the standard lines of response dataset to obtain a standard coincidence dataset; and
   reconstructing a series of medical images of the subject using the standard coincidence dataset.

15. The method of claim 14, wherein the radionuclide emits positrons and at least one prompt gamma ray upon decay.

16. The method of claim 14, wherein the multiple coincidence events are triple coincidence events.

17. The method of claim 14, wherein the multiple coincidence event dataset includes a first multiple coincidence event dataset corresponding to n-tuple coincidence events, wherein n is greater than two, and a second multiple coincidence event dataset corresponding to (n−1)-tuple coincidence events.

18. The method of claim 14, wherein the multiple coincidence events comprise groups of double coincidence events, wherein each group is at least comprised of a first pair of double coincidence events and a second pair of double coincidence events, wherein one common coincidence event belongs to both pairs of double coincidence events.

19. An emission tomography system for acquiring a series of medical images of a subject after administration of a radionuclide to the subject, wherein the radionuclide decays emitting gamma rays including positrons and at least one prompt gamma ray, the system comprising:
- a plurality of detectors configured to be arranged about the subject to acquire gamma rays emitted from the subject as a result of the radionuclide administered to the subject and communicate signals corresponding to acquired gamma rays;
- a data processing system configured to
  - receive the signals from the plurality of detectors,
  - determine, from the signals from the plurality of detectors, a double coincidence event dataset and a multiple coincidence event dataset,
  - separate the multiple coincidence event dataset into at least one of standard lines of response dataset and a non-standard lines of response dataset,
  - obtain a correction for the double coincidence event dataset based on at least one of the non-standard lines of response dataset and the standard lines of response dataset; and
- a reconstruction system configured to receive the double coincidence dataset and the correction and reconstruct therefrom a series of medical images of the subject.

20. The system of claim 19, wherein the reconstruction system is configured to reconstruct the series of medical images using an iterative reconstruction process and using the double coincidence dataset and the correction as inputs to the iterative reconstruction process.

21. The system of claim 19, wherein separating the multiple coincidence event dataset into the standard lines of response dataset and the non-standard lines of response dataset includes:

- identifying multiple coincidence events comprising at least two projected lines of response in a field of view of the subject,
- applying weights to each of the at least two projected lines of response,
- updating the weights based on relative occurrence rates of aggregated weights along each of the at least two projected lines of response,
- determining the standard lines of response dataset as a distribution of the at least two projected lines of response with the updated weights applied, and
- determining the non-standard lines of response dataset as a distribution of the at least two projected lines of response with one minus the updated weights applied.

22. The system of claim 19 and further comprising adding the standard lines of response dataset to the standard coincidence dataset.

23. The system of claim 19, wherein the multiple coincidence event dataset is a triple coincidence event dataset.

24. The system of claim 19, wherein the correction is a background correction.

25. The system of claim 19, wherein the multiple coincidence event dataset is comprised of groups of double coincidence events, wherein each group is at least comprised of a first double coincidence and a second double coincidence that share a common detected event.

* * * * *

UNITED STATES PATENT AND TRADEMARK OFFICE
CERTIFICATE OF CORRECTION

PATENT NO. : 10,215,864 B2
APPLICATION NO. : 14/902084
DATED : February 26, 2019
INVENTOR(S) : Joaquikn L. Herraiz et al.

Page 1 of 1

It is certified that error appears in the above-identified patent and that said Letters Patent is hereby corrected as shown below:

In the Claims

Column 16, Claim 17, Line 56, "(n-1)" should be --(n+1)--.

Signed and Sealed this
Twenty-third Day of April, 2019

Andrei Iancu
*Director of the United States Patent and Trademark Office*